United States Patent [19]
Adams et al.

[11] Patent Number: 5,158,079
[45] Date of Patent: Oct. 27, 1992

[54] IMPLANTABLE DEVICE FOR PREVENTING TACHYARRHYTHMIAS

[75] Inventors: John M. Adams, Issaquah; Clifton A. Alferness, Redmond, both of Wash.

[73] Assignee: InControl, Inc., Redmond, Wash.

[21] Appl. No.: 660,541

[22] Filed: Feb. 25, 1991

[51] Int. Cl.$^5$ ............................................. A61N 1/39
[52] U.S. Cl. .................................. 128/419 D; 128/705
[58] Field of Search ............ 128/419 PG, 419 D, 70 S

[56] References Cited

U.S. PATENT DOCUMENTS

| | | | |
|---|---|---|---|
| 3,937,226 | 2/1976 | Funke | 128/419 D |
| 4,088,140 | 5/1978 | Rockland et al. | 128/419 PG |
| 4,384,585 | 5/1983 | Zipes | 128/419 D |
| 4,403,614 | 9/1983 | Engle et al. | 138/419 D |
| 4,554,922 | 11/1985 | Prystowsky et al. | 128/419 PG |
| 4,790,317 | 12/1988 | Davies | 128/419 D |
| 4,928,688 | 5/1990 | Mower | 128/419 PG |

*Primary Examiner*—Kyle L. Howell
*Assistant Examiner*—Scott M. Getzow
*Attorney, Agent, or Firm*—Foley & Lardner

[57] ABSTRACT

An implantable device prevents tachyarrhythmias of a human heart which has arrhythmogenic tissue such as a myocardial infarction site. The device includes a plurality of electrodes configured for electrical contact with the heart and for placement in proximity to the arrhythmogenic tissue and a sensor including a single sensing electrode for sensing electrical activations of one chamber of the heart. A pulse generator coupled to the plurality of electrodes and responsive to the sensor provides the plurality of electrodes with an electrical pulse during each sensed electrical activation.

16 Claims, 4 Drawing Sheets

IMPLANTABLE DEVICE FOR PREVENTING TACHYARRHYTHMIAS

BACKGROUND OF THE INVENTION

The present invention generally relates to a device for preventing tachyarrhythmias of the human heart. The present invention more particularly relates to such a device which prevents tachyarrhythmias in a human heart which has arrhythmogenic tissue and more particularly, a site or region of myocardial infarction.

Myocardial infarction has long been directly associated with tachyarrhythmias of the human heart such as, ventricular tachyarrhythmias. Myocardial infarctions are areas of dying or dead heart muscle tissue resulting from obstruction of the blood vessels normally supplying blood to the site or region of an infarct. These infarctions create tissue beds which contain regions of tissues which do not die and are a substrate for the existence of re-entrant arrhythmias such as ventricular tachycardia. These surviving arrhythmogenic tissues can be on the epicardium, the endocardium, or both. Once this substrate has been formed by an infarction, an arrhythmia such as ventricular tachycardia can be initiated by heart activity such as a premature ventricular contraction.

It has been shown that premature stimuli can induce sustained re-entrant ventricular tachycardia in an animal model of chronic, transmural infarction. The recovery of refractoriness as well as the patterns of activation were mapped during the initiation and maintenance of sustained monomorphic ventricular tachycardia. In this model, re-entry paths were shown to be present in the surviving tissue on the epicardium.

Electrophysiological testing in patients with a history of myocardial infarction has demonstrated that they may also have this substrate of vulnerability to ventricular tachycardia. In these patients, a catheter is typically advanced down a vein or artery until it is inside one of the ventricles of the heart. A train of electrical stimuli or pulses are then applied to the heart through this catheter. These are applied at fixed intervals such as 300 milliseconds. Following the last of the stimuli, a premature stimulus is applied at a shorter interval. This process is repeated at progressively shorter (premature) intervals until ventricular tachycardia is induced or until the premature stimulus nor longer captures the heart. Such electrophysiological testing thus elucidates the substrate that is susceptible to the induction of ventricular tachycardia.

One device has been proposed for preventing ventricular tachycardia in U.S. Pat. No. 3,937,226. The device described in that patent includes a plurality of electrodes which are placed at selected points on a heart. The plurality of electrodes are paced in response to the sensing of an activation or an R Wave on any of the electrodes. In a second embodiment described in this patent, separate pluralities of sensing and stimulation electrodes are used. As a result of this device operation, the disparity of activation and therefore recovery of the tissues in the various regions near the electrodes were made more uniform. However, this device requires a large number of electrodes and the placement of the electrodes was not based on measured activations, the existence of an infarct site or region, or the location of such an infarct site or region.

A similar system is also described in U.S. Pat. No. 4,088,140. As described in this patent, this system provides pacing either to the plurality of electrodes when a premature activation is sensed on any one of the electrodes or to less than all of the electrodes when an escape interval is exceeded since the last sensing of an R Wave. This system serves to make the activation and the resultant refractoriness more uniform for premature beats or premature ventricular contractions but does not effect the myocardial infarction substrate from beats at normal intervals.

Neither of the above mentioned systems focused on the relationship between the size and location of a myocardial infarction and the propensity for induction o ventricular tachycardia due to a myocardial infarction. As a result, there is a need in the art for an improved implantable device and method for preventing tachyarrhythmias of a human heart which has arrhythmogenic tissue such as a myocardial infarction.

SUMMARY OF THE INVENTION

The present invention provides an implantable device for preventing tachyarrhythmias of a human heart which has arrhythmogenic tissue. The device includes a plurality of electrodes configured for electrical contact with the heart, the electrodes being arranged for placement in proximity to the arrhythmogenic tissue, sensing means including a single sensing electrode for sensing electrical activations of one chamber of the heart, and generator means coupled to the sensing means and the plurality of electrodes for providing the plurality of electrodes with an electrical pulse during each sensed electrical activation responsive to the sensing means.

The invention further provides an implantable device for preventing tachyarrhythmias of a human heart occasioned by the presence of at least one myocardial infarction site. The device includes a plurality of electrodes configured for electrical contact with the heart and being arranged for placement about the myocardial infarction site, sensing means including a single sensing electrode configured for electrical contact with one chamber of the heart for sensing electrical activations of the one chamber, and pulse generating means responsive to the sensing means and coupled to the plurality of electrodes for providing the plurality of electrodes with an electrical pulse during the electrical activations sensed by the sensing means.

The device may further include means for timing the time from an immediately preceding sensed electrical activation to a presently sensed electrical activation, means for causing the generating means to provide the electrical pulse to the plurality of electrodes when the time between the immediately preceding sensed electrical activation and the presently sensed electrical activation is greater than a first predetermined time period and less than a second predetermined time period and for causing the generating means to provide the electrical pulse to the plurality of electrodes in the absence of a sensed electrical activation and when the time from the immediately preceding sensed electrical activation is greater than the second predetermined time.

The device may further include means for detecting ventricular tachycardia coupled to the sensing electrode and arranged for causing the generating means to provide the plurality of electrodes with a second electrical pulse after detecting a ventricular tachycardia and during one of the sensed electrical activations.

The device may further include sense amplifier means coupled to each of the plurality of electrodes for sensing heart activity at any one of the plurality of electrodes and wherein the generating means is further arranged to provide the electrical pulse to the plurality of electrodes in response to heart activity being sensed at any one of the plurality of electrodes.

The present invention further provides a method of preventing tachyarrhythmias in a human heart which has arrhythmogenic tissue. The method includes the steps of providing a plurality of electrodes configured for electrical contact with the heart, placing the electrodes in proximity to the arrhythmogenic tissue, and providing a sensing electrode. The method further includes the steps of establishing electrical contact between the sensing electrode and one chamber of the heart, sensing electrical activations in the one chamber, and applying a electrical pulse to the plurality of electrodes during each electrical activation sensed in the one chamber.

The present invention still further provides a method of preventing tachyarrhythmias in a human heart occasioned by the presence of at least one myocardial infarction site. The method includes the steps of providing a plurality of electrodes configured for electrical contact with the heart, placing the plurality of electrodes about the myocardial infarction site, and coupling a sense amplifier to the plurality of electrodes. The method further includes the steps o sensing for heart activity at the plurality of electrodes and applying an electrical pulse to the plurality of electrodes upon sensing heart activity at any one of the plurality of electrodes.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DESCRIPTION OF THE PREFERRED EMBODIMENTS

There are two physiologic factors that enter into the effective treatment of a human heart prone to tachyarrhythmias due to having arrhythmogenic tissue such as a region of myocardial infarction. The first is that the spared or surviving tissue is a thin layer overlying a large transmural infarction. If the infarct is smaller and the spared tissue is thicker, the activations can be essentially three-dimensional. If the infarct is larger, the spared tissue is essentially a two-dimensional sheet of tissue. This two-dimensional spared tissue allows a long path link for re-entry and therefore a long enough activation interval to become a stable re-entrant path.

This may lead to a stable monomorphic ventricular tachycardia. The second factor is that the heart requires a trigger stimulus that must be critically timed to the previous heartbeat. When the activation of a premature beat collides with an appropriate refractoriness in the spared region, a re-entrant path of activation can result and lead to ventricular tachycardia.

In accordance with the present invention, the electrodes which apply stimulation pulses to the heart are preferably placed in electrical contact with the heart about or around the site or region of myocardial infarction. Hence, it is preferable to first locate the region of the infarct to permit the electrodes to be placed there around. There are several well known techniques for determining the location of an infarct. Once such technique is described in Movahed A, Becker LC: *Electrocardiographic changes of acute lateral wall myocardial infarction: a reappraisal based on scintigraphic localization of the infarct.* J Am Coll Cardiol 4:660, 1984. Once the infarct is located and its boundaries noted, a plurality of stimulation electrodes are implanted in the viable tissue near the border of the infarct.

Figure 1:
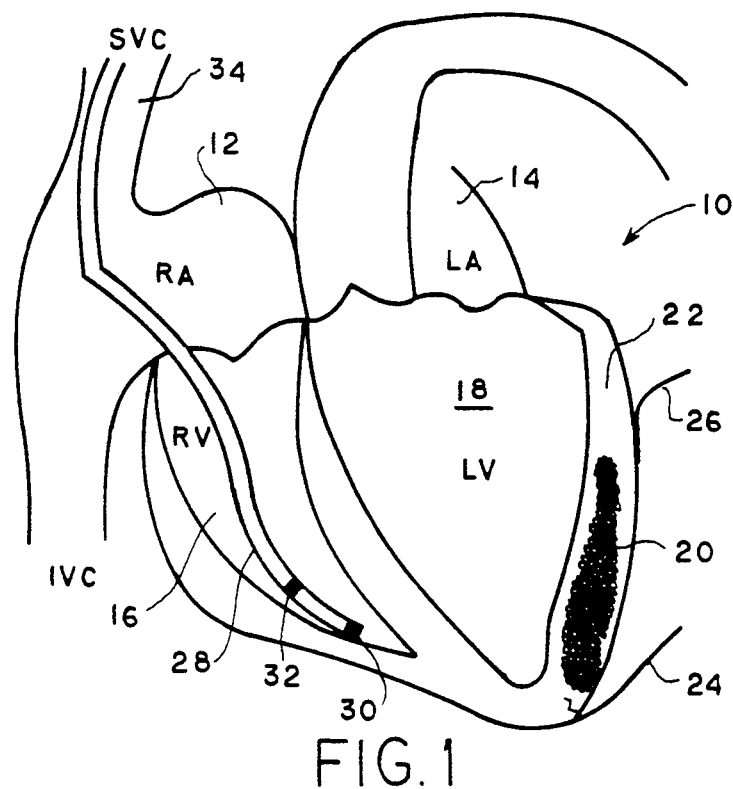
FIG. 1 is a schematic illustration of a human heart having a myocardial infarction region to be treated by an implantable device embodying the present invention.

Referring now to FIG. 1, it illustrates a human heart 10 having a right atrium 12, a left atrium 14, a right ventricle 16, and left ventricle 18. The left ventricle 18 includes a myocardial infarction region 20 within the left ventricle muscle or myocardium 22. Electrodes 24 and 26 are placed into electrical contact with the heart at opposite ends of the myocardial infarction region 20. The electrodes 24 and 26 are epicardial electrodes which preferably have a tip which may be screwed into the myocardium or heart muscle. Hence, the term "epicardial electrode" as used herein is meant to include any electrode which may be attached to the outer surface of the heart or which may be so attached and having a tip which may penetrate the epicardium into the myocardium.

Within the right ventricle 16 there is a single sensing electrode 28 for sensing electrical activations of the right ventricle chamber and thus for sensing R Waves of the heart 10. The electrode 28 includes a tip 30 and ring 32 to permit bipolar sensing of the R Waves within the right ventricle. The endocardial sensing electrode 28 is placed into the right ventricle through the superior vena cava 34, the right atrium 12, and then into the right ventricle 16.

When an activation (R Wave) is sensed by the sensing electrode 28 in the right ventricle, the electrodes 24 and 26 surrounding the myocardial infarction region 20 are simultaneously provided with an electrical pulse by a pulse generator to be described hereinafter. The pulse provided to the electrodes 24 and 26 is thus applied to the viable tissue about the myocardial infarction region 20 to effectively encircle the myocardial infarction region 20 with the stimulation and isolate the myocardial infarction region 20. This has the effect of making it unlikely for ventricular tachycardia to be initiated within the left ventricle 18 of the heart 10 due to the presence of the myocardial infarction region 20.

Figure 2:
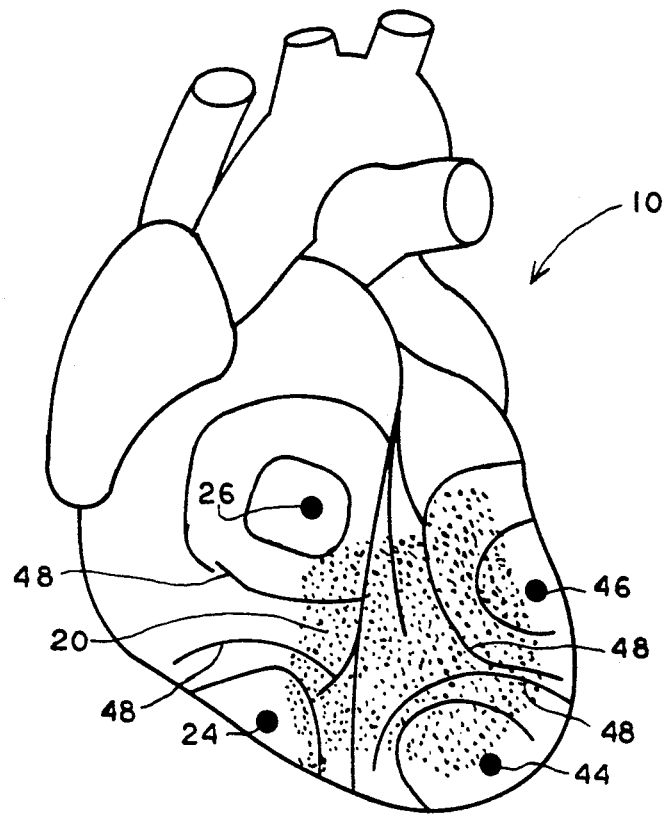
FIG. 2 is simplified perspective view of a human heart having a myocardial infarction region and illustrating the placement of a plurality of electrodes to enable the treatment of the myocardial infarction site by an implantable device embodying the present invention.

Referring now to FIG. 2, it illustrates a human heart 10 having the epicardium thereof over a myocardial infarction region 20. A plurality of epicardial electrodes 24, 26, 44 and 46 are placed into electrical contact with the heart in the viable tissue surrounding the myocardial infarction region 20. When an R Wave is detected by the single sensing electrode implanted in the right ventricle, the electrodes 24, 26, 44, and 46 are simultaneously provided with an electrical pulse which results in activation wave fronts 48 spreading out away from each of the electrodes as illustrated. These activation wave fronts collide and converge toward the center of the infarct region. This prevents the infarcted region from having its activation spread through it from any one side as would normally occur and creates a more uniform and rhythmically stable environment.

Figure 3:
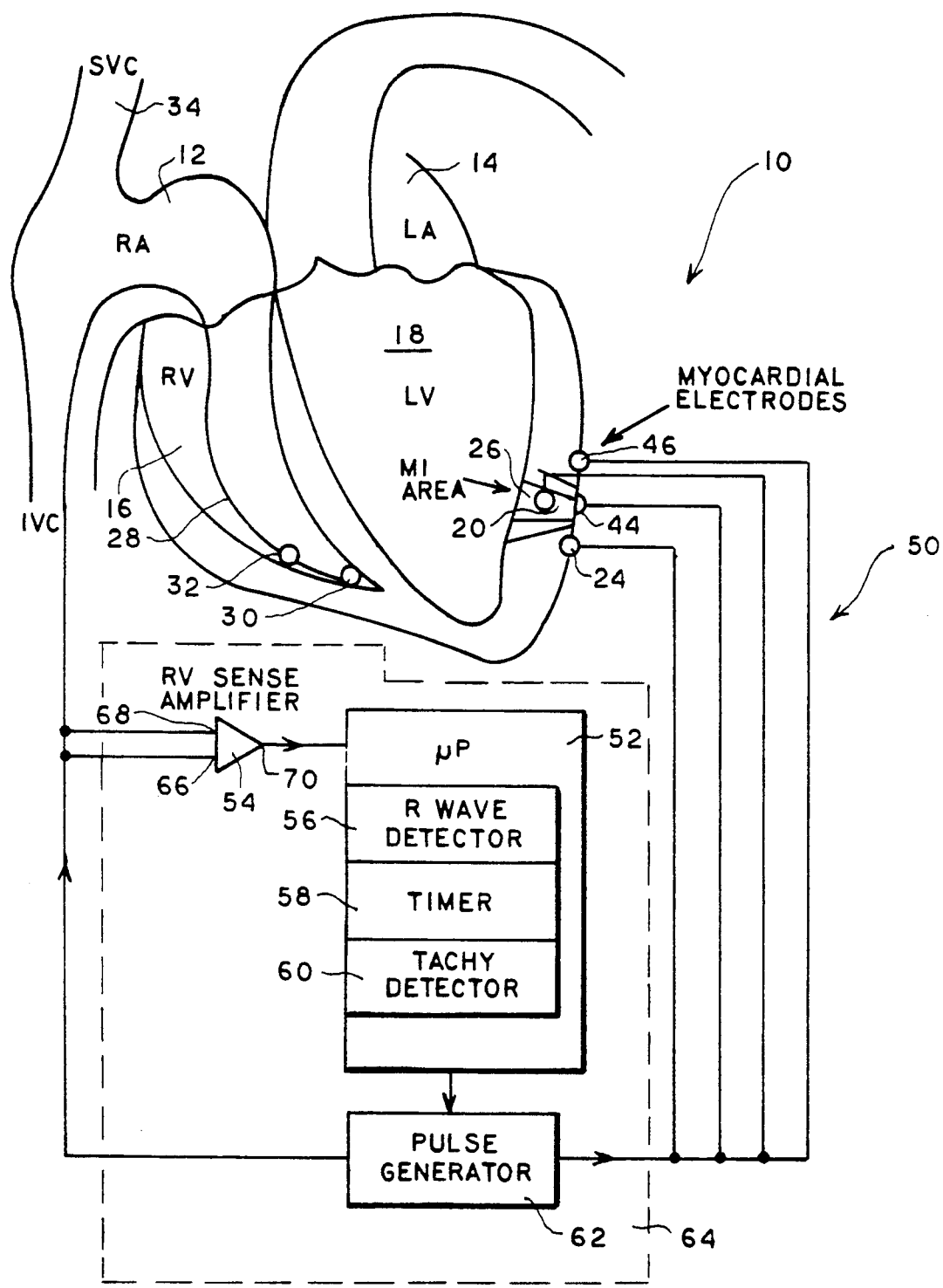
FIG. 3 is a block diagram of an implantable device embodying the present invention shown in association with a human heart in need of treatment

Referring now to FIG. 3, it illustrates an implantable device 50 associated with a human heart 10 under treatment. The device 50 includes the plurality of electrodes 24, 26, 44, and 46, the single sensing electrode 28, a microprocessor 52, and a sense amplifier 54. The device further includes an R Wave detector 56, a timer 58, a tachycardia detector 60, and a pulse generator 62. The microprocessor 52, sense amplifier 54, R Wave detector 56, timer 58, tachycardia detector 60, and pulse generator 62 are all enclosed in a metal case 64 which is implantable in the human body in a well known manner.

The sense amplifier 54 includes a pair of inputs 66 and 68 which are coupled to the ring and tip poles 32 and 30 respectively of the sensing electrode 28. The sensing electrode 28 in accordance with this embodiment is placed into the right ventricle by being guided through the inferior vena cava, the right atrium 12, and into the right ventricle 16. The inputs 66 and 68 of sense amplifier 54 enable the bipolar sensing of right ventricle electrical activations or R Waves. The sense amplifier 54 provides an output at output 70 upon sensing each R Wave which is utilized by the R Wave detector 56.

The timer 58 is provided to time the time between the last or immediately preceding sensed R Wave and the current time or the time in which a present R Wave is detected. The tachycardia detector 60, as will be seen hereinafter, is utilized for detecting a tachycardia, such as a ventricular tachycardia in this embodiment, upon being activated when a tachycardia is suspected to be present.

The pulse generator 62 is coupled to the microprocessor for receiving control signals for controlling when a stimulating electrical pulse is to be outputed by the pulse generator 62, for controlling which electrodes are to receive the electrical pulse, and for controlling the magnitude of the energy in the stimulating electrical pulse. As will be seen hereinafter, when the heart 10 is in its normal rhythm, upon each R Wave being sensed, an electrical pulse is applied to only the electrodes 24, 26, 44, and 46 to prevent the infarcted region 20 from having its activation spread through it from anyone side as would normally occur. The stimulating electrical pulse may also be applied to the sensing electrode 28 in the absence of a sensed R Wave or contraction and when the time from the immediately preceding sensed contraction or R Wave is greater than a predetermined time period or escape interval. In addition, the stimulating pulse is applied, as in this latter case, to all of the electrodes, electrodes 24, 26, 44, 46, and 28 when a tachycardia has been detected. This latter pulse however is at a much higher energy than the other stimulating electrical pulses. For example, the first mentioned pulses may have energies of 25 microjoules per electrode while the second mentioned electrical pulse may have a total energy on the order of 1.5 joules for arresting a tachycardia.

Figure 4:
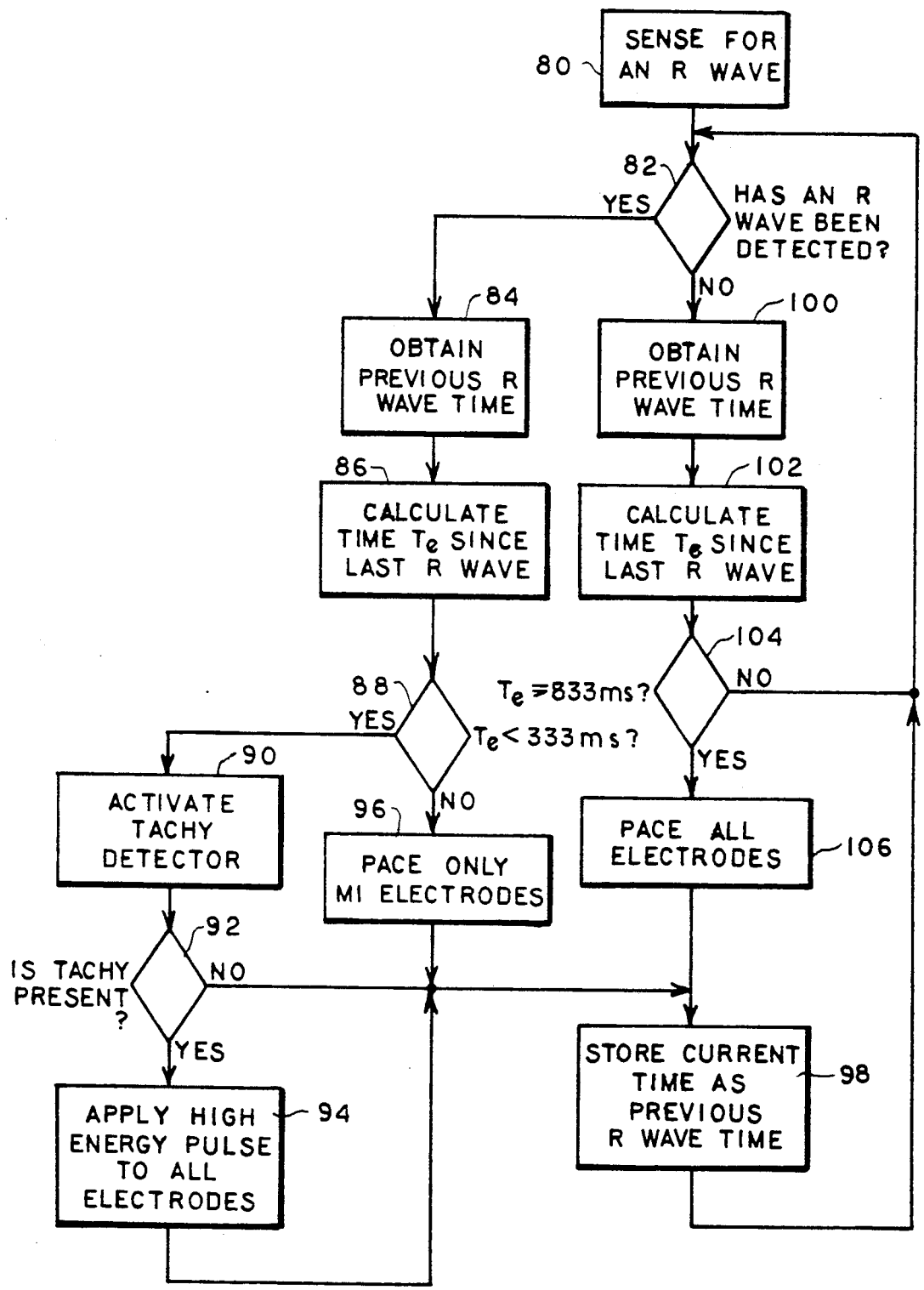
FIG. 4 is a flow diagram illustrating the manner in which the device of FIG. 3 may be implemented in accordance with a preferred embodiment of the present invention.

Referring now to FIG. 4, it provides a flow chart illustrating the manner in which the device 50 of FIG. 3 may be implemented for practicing the present invention in accordance with this preferred embodiment. As will be noted from step 80, the R Wave detector is caused by the microprocessor to continuously sense for an R Wave emanating from the right ventricle. As previously mentioned, the R Waves in the right ventricle 16 are sensed by the electrode 28 which provides a signal for each sensed R Wave to the sense amplifier 54. The sense amplifier 54 provides an output at output 70 for each sensed R Wave which is then conveyed to the R Wave detector 56.

In step 82, the microprocessor determines whether an R Wave has been detected. If an R Wave has been detected, the processor proceeds to step 84 wherein it obtains the time in which the previous R Wave had been detected. Then, in step 86, the processor calculates the time ($T_e$) which has elapsed since the last R Wave was detected. Then, in step 88, the processor determines whether the elapsed time is less than a first predetermined time period of, for example, 250 milliseconds. If the elapsed time is less than 250 milliseconds, a ventricular tachycardia is suspected and the processor will proceed to step 90 for activating the tachycardia detector 60.

Tachycardia detectors are well known in the art and generally require more than one cardiac cycle to determine whether a tachycardia is present. After a predetermined number of cycles, the processor in step 92 determines whether a tachycardia is present. If a tachycardia is present, the processor proceeds to step 94 to issue control signals to the pulse generator 62 to cause the pulse generator to provide the high energy pulse to all of the electrodes in an effort to terminate the tachycardia. Preferably, the high energy electrical pulse is applied to all of the electrodes in synchronism with a detected R Wave (during an R Wave). In general, the duration of an R Wave is on the order of 60 to 70 milliseconds. It is therefore preferred to provide the pulse to the electrodes to terminate the tachycardia during the 60 to 70 millisecond duration period of the R Waves. Such timing of the electrical pulse is preferably directly timed from the signals provided by the R Wave detector 56. After providing the high level pulse, the microprocessor then proceeds to step 98 for storing the current time in the previous R Wave time and then returns to step 82.

If in step 88 it was determined that the elapsed time was greater than 333 milliseconds, the processor would then proceed to step 96 to issue the control signals to the pulse generator 62 and to cause the pulse generator to pace only electrodes 24, 26, 44, and 46. The electrical pulse applied to the electrodes surrounding the myocardial infarction region or site is preferably applied also during the sensed electrical activation or R Wave. Such synchronous pacing is readily obtained in as much as the time it would take for an R Wave to be detected in step 82 to the time when the pulse generator 62 is ready to provide its electrical output would be on the order of 30 milliseconds which is well within the 60 to 70 milliseconds duration period in which a electrical activation or R Wave exists. After pacing electrodes 24, 26, 44 and 46, the processor proceeds to step 98 to store the current time as the previous R Wave time and then returns to step 82.

If in step 82 the processor determines that a new R Wave has not yet been detected, it proceeds to step 100 to obtain the time in which the previous R Wave had been detected. It then proceeds to step 102 to calculate the elapsed time since the last R Wave was detected. It then proceeds to step 104 to determine whether the elapsed time is equal to or greater than a second predetermined time period of, for example, 833 milliseconds. If the elapsed time is equal to or greater than the second predetermined time period, this will indicate that the heart rate is slower than a desired rate and that an escape interval has elapsed. As a result, the microprocessor proceeds to step 106 to provide the necessary control signals to pulse generator 62 to cause the pulse generator to immediately provide the electrical stimulating pulse to all of the electrodes including the plurality of electrodes 24, 26, 44, and 46, and in addition, the sensing electrode 28. While applying the bradycardia pacing pulse to the sensing electrode 28 is disclosed herein in accordance with this preferred embodiment, it may be eliminated if battery conservation is desired, so that only the plurality of electrodes 24, 26, 44, and 46 are paced. Either approach provides the bradycardia pacing to the heart on a demand basis. After issuing the control signals to the pulse generator 62, the processor then proceeds to step 98 to store the current time as the previous R Wave time and then returns to step 82.

As a result of the foregoing, it can been seen that the device of FIG. 3 is arranged to provide a stimulating electrical pulse only to the myocardial infarction electrodes 24, 26, 44, and 46 when the elapsed time between sensed R Waves is greater than the first predetermined time period of, for example, 250 milliseconds and less than a second predetermined time period, of, for example, 833 milliseconds, or in other words, when the heart is maintaining its normal rhythm. However, if the heart rhythm slows so that a new R Wave is not sensed within the second predetermined time period of, for example, 833 milliseconds, the microprocessor will provide the suitable control signals to the pulse generator 62 to cause the pulse generator to provide the stimulating electrical pulse to the plurality of electrodes 24, 26, 44, and 46 and may also apply the pulse to the sensing electrode 28 in the right ventricle 16 to provide bradycardia pacing. Lastly, if the elapsed time between R Waves is less than the first predetermined time period of, for example, 333 milliseconds, a ventricular tachycardia is suspected and a tachycardia detector is activated for eventually causing a high energy pulse to be applied to all of the electrodes during an R Wave to terminate the tachycardia if one is present.

Figure 5:
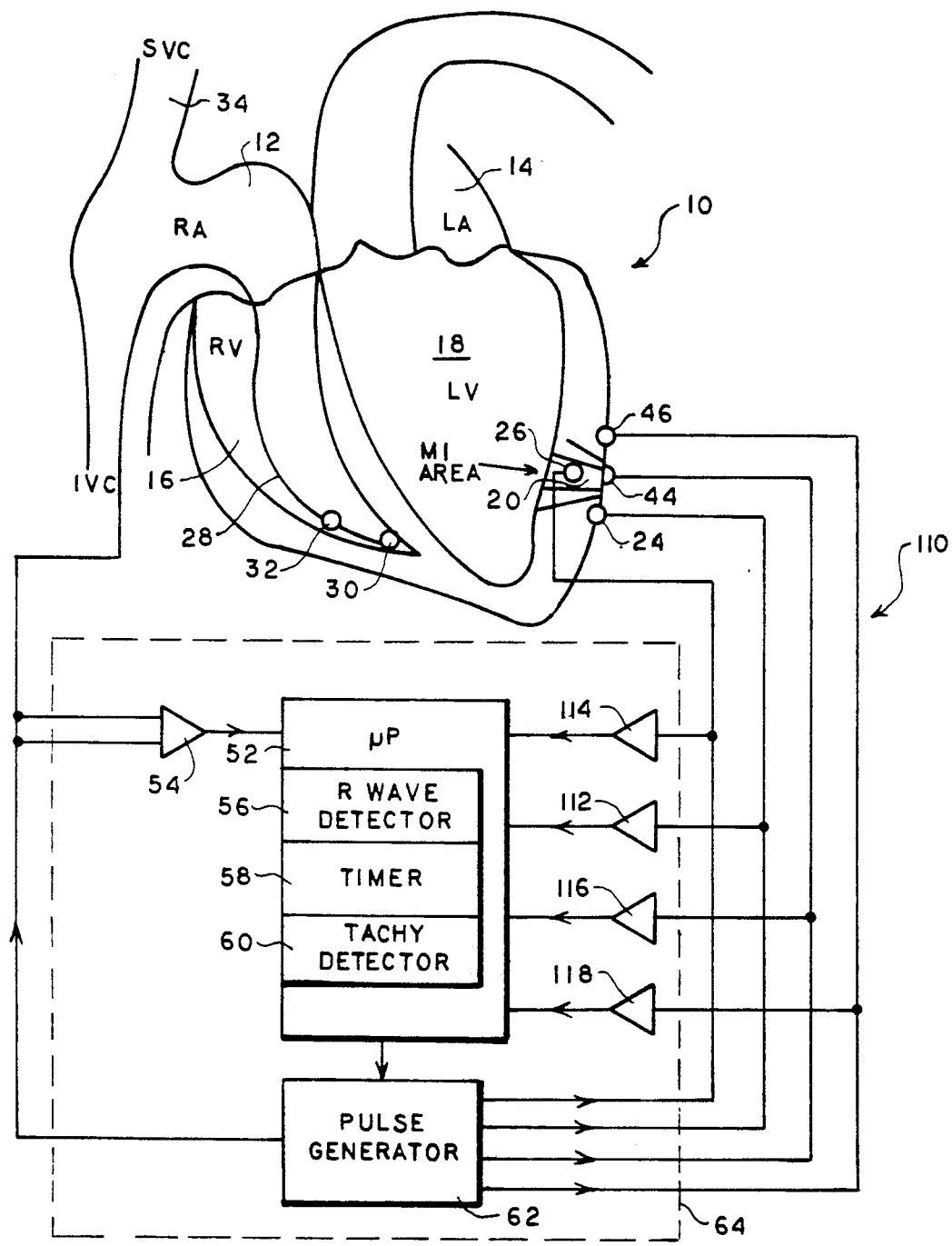
FIG. 5 is a block diagram of another implantable device embodying the present invention in association with a human heart in need of treatment.

Referring now to FIG. 5, it illustrates another device 110 embodying the present invention for preventing tachyarrhythmias of a human heart. The device 110 incorporates all of the modalities of the device 50 of FIG. 3 and as a result, identical numerals are utilized to identify identical elements. The difference between the device 110 of FIG. 5 and the device 50 of FIG. 3 is that the device 110 includes a sense amplifier associated with each of the myocardial infarction electrodes. More specifically, device 110 includes sense amplifiers 112, 114, 116, and 118 coupled to electrodes 24, 26, 44, and 46 respectively. This enables heart activity to be detected by the microprocessor 52 from the electrodes 24, 26, 44, and 46.

Each of the amplifiers 112, 114, 116, and 118 is coupled to the microprocessor 52. When any one of the electrodes 24, 26, 44, and 46 detects an activation or heart activity, the microprocessor provides the pulse generator 62 with the set of control signals which will cause the pulse generator to provide the stimulating electrical pulse simultaneously to only the electrodes 24, 26, 44, and 46. The device 110 thus has the advantage that refractoriness in the arrhythmogenic region 20 containing the myocardial infarction is made more uniform for premature ventricular contractions as well as for a normal heart beat. Of course, the addition of the sense amplifiers 112, 114, 116 and 118 requires additional power consumption and other circuitry not required in the device 50 of FIG. 3.

While particular embodiments of the present invention have been shown and described, modifications may be made, and it is therefore intended to cover in the appended claims all such changes and modifications which fall within the true spirit and scope of the invention.

What is claimed is:

1. An implantable device for preventing tachyarrhythmias of a human heart which has arrhythmogenic tissue, said device comprising:

a pluarilty of electrodes configured for electrical contact with the heart, said electrodes being arranged for placement in proximity to said arrhythmogenic tissue;

sensing means including a single sensing electrode for sensing electrical activations of one chamber of the heart;

generator means coupled to said plurality of electrodes for providing said plurality of electrodes with an electrical pulse during each said sensed electrical activation responsive to said sensing means;

said plurality of electrodes being configured for electrical contact with the left ventricle of the heart and about said arrhythmogenic tissue and said sensing means single sensing electrode being configured for electrical contact with the right ventricle of the heart;

means for detecting ventricular tachycardia coupled to said sensing electrode and arranged for causing said generator means to provide said plurality of electrodes with a second electrical pulse after detecting ventricular tachycardia and during one of said sensed electrical activations; and said electrical pulse being on the order of 25 microjoules per electrode and said second electrical pulse being on the order of 1.5 joules.

2. An implantable device for preventing tachyarrhythmias of a human heart occasioned by the presence of at least one myocardial infarction site, said device comprising:

a plurality of electrodes configured for electrical contact with the heart, said electrodes being arranged for placement about said myocardial infarction site;

sensing means including a single sensing electrode configured for electrical contact with one chamber of the heart for sensing electrical activations of said one chamber;

pulse generating means responsive to said sensing means and coupled to said plurality of electrodes for providing said plurality of electrodes with an electrical pulse during the electrical activations sensed by said sensing means;

means for timing the time from an immediately preceding sensed electrical activation to a presently sensed electrical activation;

first means for causing said generating means to provide said electrical pulse to said plurality of electrodes when the time between said immediately preceding sensed electrical activation and said presently sensed electrical activation is greater than a first predetermined time period and less than a second predetermined time period;

second means for causing said generating means to provide said electrical pulse to said plurality of electrodes in the absence of a sensed electrical activation and when the time from said immediately preceding sensed electrical activation is greater than said second predetermined time period; and means for detecting ventricular tachycardia coupled to said sensing electrode and arranged for causing said generating means to provide said plurality of electrodes with a second electrical pulse after detecting a ventricular tachycardia and during one of said sensed electrical activations.

3. A device as defined in claim 2 wherein said device is arranged for activating said ventricular tachycardia detector when the time between said immediately preceding sensed electrical activation and said presently sensed electrical activation is less than said first predetermined time period.

4. A device as defined in claim 3 wherein said electrical pulse is on the order of 25 microjoules per electrode and wherein said second electrical pulse is on the order of 1.5 joules.

5. A device as defined in claim 2 wherein said plurality of electrodes include four electrodes.

6. A method of preventing tachyarrhythmias in a human heart which has arrhythmogenic tissue, said method comprising the steps of:

providing a plurality of electrodes configured for electrical contact with the heart;

placing said electrodes in proximity to said arrhythmogenic tissue;

providing a sensing electrode;

establishing electrical contact between said sensing electrode and one chamber of the heart;

sensing electrical activations in said one chamber; and applying an electrical pulse to said plurality of electrodes during each electrical activation sensed in said one chamber.

7. A method as defined in claim 6 wherein said placing step includes placing said plurality of electrodes about said arrhythmogenic tissue.

8. A method as defined in claim 6 wherein said placing step includes placing said plurality of electrodes in electrical contact with the left ventricle of the heart and about said arrhythmogenic tissue and wherein said establishing step includes establishing electrical contact between said sensing electrode and the right ventricle of the heart.

9. A method as defined in claim 8 wherein said plurality of electrodes are placed on the epicardium of the heart.

10. A method as defined in claim 9 wherein said sensing electrode is placed within the right ventricle of the heart.

11. A method as defined in claim 8 wherein said applying step includes applying said electrical pulse also to said sensing electrode.

12. A method as defined in claim 11 further including the steps of timing the time from an immediately preceding sensed electrical activation to a presently sensed electrical activation, applying said electrical pulse to only said plurality of electrodes when the time between said immediately preceding sensed electrical activation and said presently sensed electrical activation is greater than a first predetermined time period and less than a second predetermined time period and applying said electrical pulse to said plurality of electrodes in the absence of a sensed electrical activation and when the time from said immediately preceding sensed electrical activation is equal to or greater than said second predetermined time period.

13. A method as defined in claim 8 further including the steps of detecting ventricular tachycardia at said sensing electrode and applying a second electrical pulse to said plurality of electrodes during one of said sensed electrical activations and after detecting ventricular tachycardia.

14. A method as defined in claim 13 wherein said electrical pulse is on the order of 25 microjoules per electrode and wherein said second electrical pulse is on the order of 1.5 joules.

15. A method as defined in claim 8 further including the steps of coupling a sense amplifier to each of said plurality of electrodes, sensing for heart activity at said plurality of electrodes, and applying said electrical pulse to said plurality of electrodes upon sensing heart activity at any one of said plurality of electrodes.

16. A method of preventing tachyarrhythmias in a human heart occasioned by the presence of at least one myocardial infarction site, said method comprising the steps of:

providing a plurality of electrodes configured for electrical contact with the heart;

placing said plurality of electrodes about said myocardial infarction site;

coupling a sense amplifier to said plurality of electrodes;

sensing for heart activity at said plurality of electrodes; and applying an electrical pulse to said plurality of electrodes upon sensing heart activity at any one of said plurality of electrodes.

* * * * *